(12) United States Patent
Hall-Stoodley et al.

(10) Patent No.: US 7,871,791 B2
(45) Date of Patent: Jan. 18, 2011

(54) BIOFILM PREPARATION USING POTASSIUM PERMANGANATE

(75) Inventors: Luanne Hall-Stoodley, Wexford, PA (US); Paul Stoodley, Wexford, PA (US)

(73) Assignee: Allegheny-Singer Research Institute, Pittsburgh, PA (US)

( * ) Notice: Subject to any disclaimer, the term of this patent is extended or adjusted under 35 U.S.C. 154(b) by 230 days.

(21) Appl. No.: 11/655,504

(22) Filed: Jan. 18, 2007

(65) Prior Publication Data

US 2008/0176265 A1   Jul. 24, 2008

(51) Int. Cl.
*G01N 1/30* (2006.01)
*G01N 21/76* (2006.01)
*A01N 59/16* (2006.01)

(52) U.S. Cl. .................. 435/40.5; 436/172; 424/640
(58) Field of Classification Search .................. None
See application file for complete search history.

(56) References Cited

U.S. PATENT DOCUMENTS 6,569,615 B1 * 5/2003 Thatte et al. .................. 435/1.1

2003/0079758 A1 * 5/2003 Siegel et al. .................... 134/3
2005/0037451 A1 * 2/2005 Chen et al. ..................... 435/34
2006/0275847 A1   12/2006 Goodyear et al.

FOREIGN PATENT DOCUMENTS

WO   WO 03/011347 A1   2/2003

OTHER PUBLICATIONS

EPA Guidance Manual: Alternative Disinfectants and Oxidants; Chapter 5, Apr. 1999, pp. 1-15 www.epa.gov/ogwdw/mdbp/pdf/alter/chapt_5.pdf ,downloaded Nov. 19, 2008.*
Whitchurch, Cynthia B.; Tolker-Nielsen, Tim; Ragas, Paula C.; Mattick, John S., "Extracellular DNA Required for Bacterial Biofilm Formation," www.sciencemag.org, Science, (vol. 295), (p. 1487), (Feb. 22, 2002).
Koerstgens V. et al., "Influence of Calcium Ions on the Mechanical Properties of a Model Biofilm of Mucoid *Pseudomonas aeruginosa*," Water Science and Technology, vol. 43 ( No. 6), pp. 49-57, (2001).

* cited by examiner

*Primary Examiner*—Rebecca E. Prouty
*Assistant Examiner*—Paul C. Martin
(74) *Attorney, Agent, or Firm*—Pepper Hamilton LLP

(57) ABSTRACT

A method for preparing a biofilm includes the steps of rinsing the biofilm. There is the step of staining the biofilm with potassium permanganate and water.

9 Claims, 3 Drawing Sheets

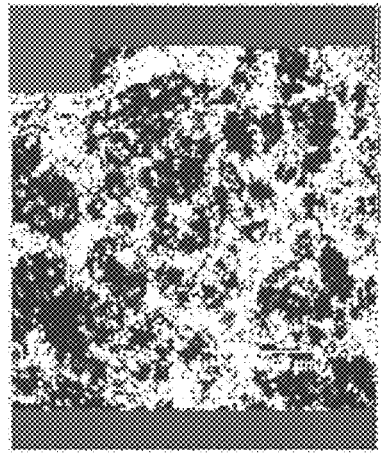 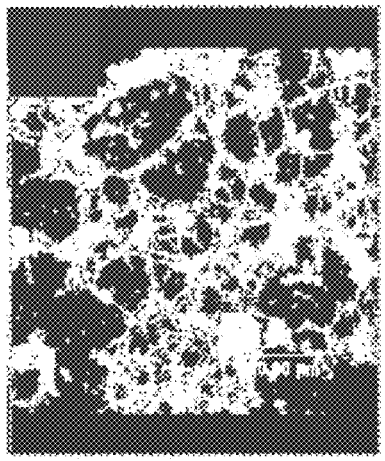 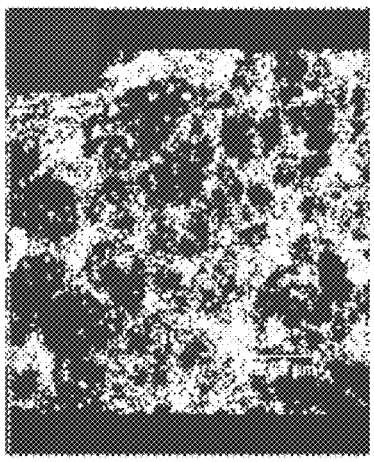
*FIG.3A*  *FIG.3B*  *FIG.3C*
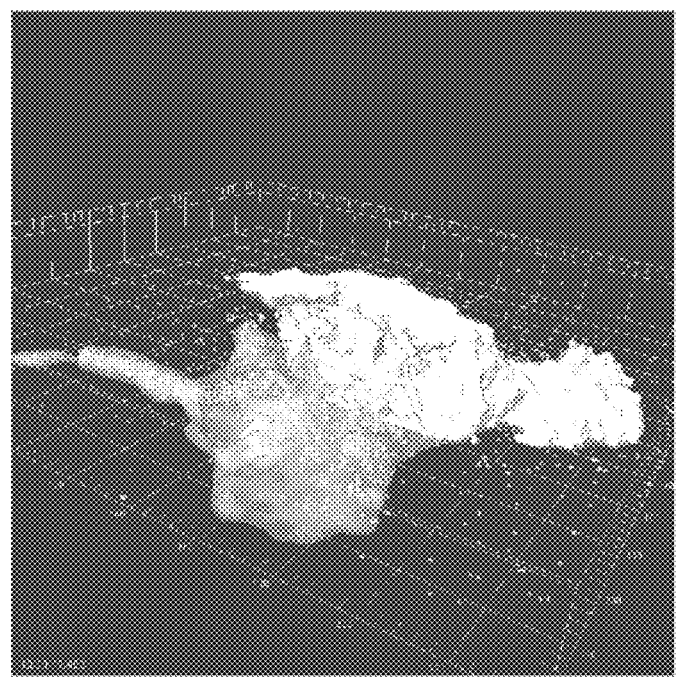
*FIG.4*

BIOFILM PREPARATION USING POTASSIUM PERMANGANATE

FIELD OF THE INVENTION

The present invention is related to the preparation of a biofilm. More specifically, the present invention is related to the preparation of a biofilm for visualization, contrast enhancement, or quantification using potassium permanganate.

BACKGROUND OF THE INVENTION

Currently, there is no generic stain for the slime matrix and it often goes undetected. 1) biofilms are important in medical and dental infections, as well as industrial biofouling, 2) the EPS matrix is a hallmark characteristic of microbial biofilms and 3) the control and killing of biofilm bacteria requires different strategies than those planktonic (or single) cells. Microscopic detection of biofilm on, or associated with, surfaces is useful for basic research and has application in clinical diagnostics.

Current technologies for staining the biofilm EPS matrix are indicated in Table 1.

TABLE 1

| Reagent | Target | Limitation |
| --- | --- | --- |
| Lectins | Stains specific sugar residues in the matrix. | There are 100s of lectins and different types of sugars in biofilm slime, therefore whether any particular one may work is hit or miss. |
| Calcuflour | Unknown - is used to stain the cell wall of fungi. | Good for only a few types of biofilm. |
| Pico Green and other nucleic acid stains | Nucleic acid in the matrix | Nucleic acids are often a small component of the slime matrix. Also since bacteria themselves stain with these stains, the brightness tends to dim out the signal from stain in the slime. |
| Ruthenium red | Acidic polysaccharides such as alginate | Good for a very specialized microscopy called "transmission electron microscopy". |
| Alcian Blue | Polysaccharides | Incompatible with fluorescent stains since it causes them to loose fluorescence (quenching). |
| Crystal violet | General stain | Incompatible with fluorescent stains since it causes them to loose fluorescence. The vast majority of biofilm research microscopy methods rely on visualizing bacteria with fluorescent stains. |
| Methylene blue | General stain | As above |

BRIEF SUMMARY OF THE INVENTION

The present invention pertains to a method for preparing a biofilm. The method comprises the steps of rinsing the biofilm. There is the step of staining the biofilm with potassium permanganate and water.

BRIEF DESCRIPTION OF THE SEVERAL VIEWS OF THE DRAWING

In the accompanying drawings, the preferred embodiment of the invention and preferred methods of practicing the invention are illustrated in which:

FIGS. 3a-c show a biofilm formed from the pathogenic bacterial species Pseudomonas aeruginosa PAO1 stained with Molecular Probes SYTO® 9 stain and Biofilm EPS Contrast Enhancer. FIG. 3A) Individual bacteria in the biofilm stained green with SYTO®9. FIG. 3B) Biofilm EPS Contrast Enhancer revealed an otherwise invisible network of interconnecting EPS. FIG. 3C) Combined image showing the juxtaposition of the bacteria and the EPS.

FIG. 4 shows a biofilm strained with the present invention.

DETAILED DESCRIPTION OF THE INVENTION

Figure 1:
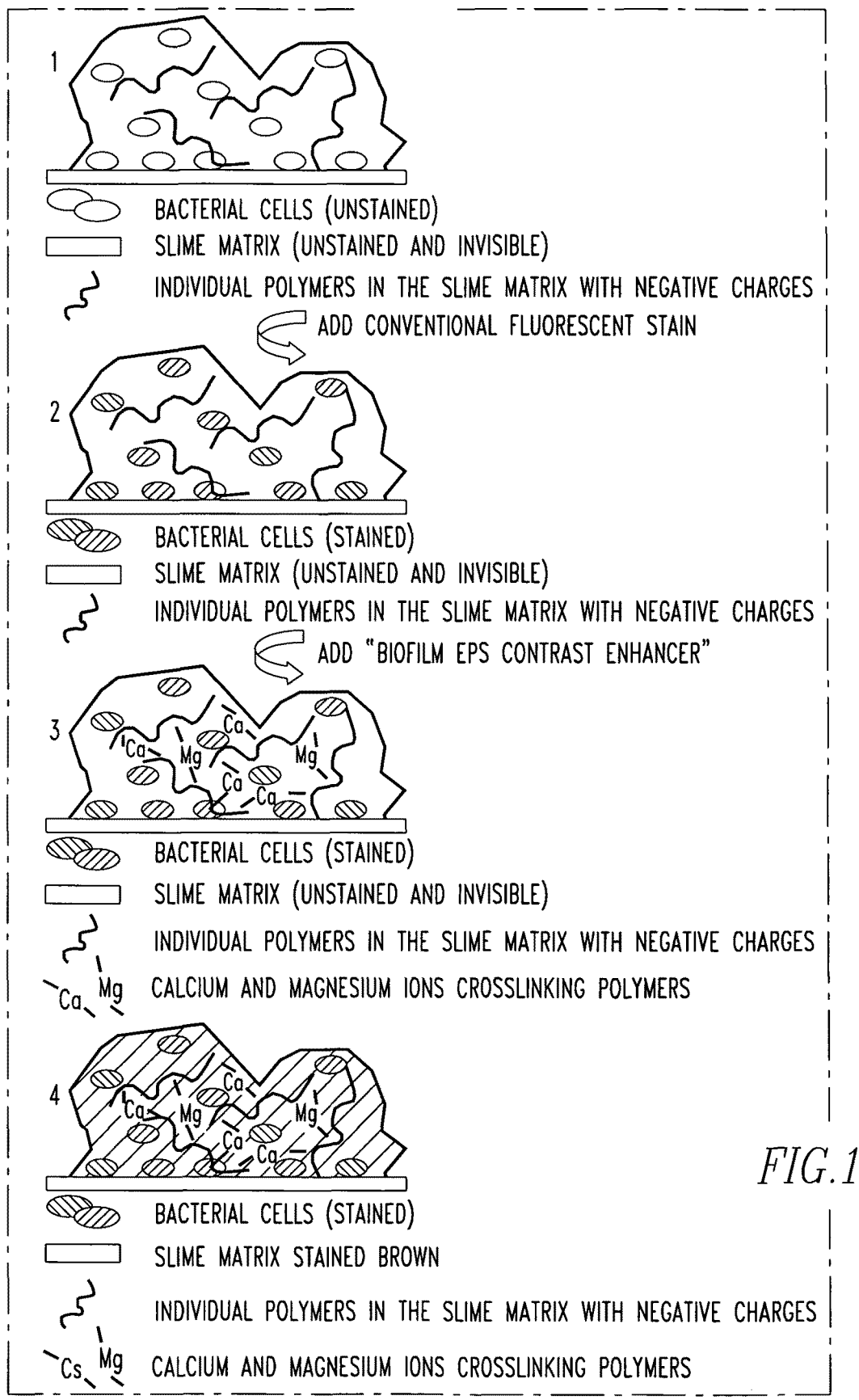
FIG. 1 shows the mechanism of action of the present invention.

The present invention pertains to a method for preparing a biofilm. The method comprises the steps of rinsing the biofilm. There is the step of staining the biofilm with potassium permanganate and water.

Preferably, there is the step of incubating the biofilm. After the staining step there is preferably the step of rerinsing the biofilm. Preferably, the rinsing step includes the step of rinsing with a solution of $CaCl_2$, $KCl$, $KH_2PO_4$, $MgCl_2.6H_2O$, $MgSO_4.7H_2O$, $NaCl$, $NaHCO_3$, and $Na_2HPO_4.7H_2O$. There is preferably the step of growing the biofilm in a multi-well plate format or flow cell format or any other biofilm reactor such as those commercially available from BioSurface Technologies and the Stovall Flow Cell from Stovall Life Sciences, inc. or any device used for growing biofilms. In addition, the preparation can be used for samples naturally containing biofilms such as clinical, industrial or environmental samples or samples from animal studies. It should be noted there are many different ways of growing biofilms. The description herein is not limited in any way to any method to grow biofilms. Also many biofilms grow naturally in infections or the environment or on industrial surfaces and so don't require any manipulated growth steps. Preferably, there is the step of visualizing the biofilm by microscopic or other methods. Preferably, there is the step of quantifying the amount of biofilm.

The present invention pertains to a stain for a biofilm comprising potassium permanganate and water.

In the operation of the preferred embodiment, the following advantages offered by the present invention is provided over these conventional techniques:

1) It is a general oxidizer therefore has the potential to work with a myriad of different types of biofilm with their different EPS compositions, which are known to be highly variable.
2) It is compatible with fluorescence.
3) It is compatible with confocal, epifluorescent and light microscopy. It provides a strong reflective signal making it ideally suited to 3D imaging with confocal microscopy using reflected mode imaging. As a contrast enhancer, it may also be used for magnetic resonance imaging (MRI) also known as nuclear magnetic resonance (NMR), scanning electron microscopy (SEM), transmission electron microscopy (TEM) and optical coherent tomography (OCT).
4) It is cheap, quick and simple to use.
5) No sample preparation is required and staining can be performed on fully hydrated clinical and laboratory specimens.
6) The principal ingredient, potassium permanganate, is currently used as a contrast stain in clinical samples containing mycobacteria and so is established as a microscopy stain. However, it has not been used as a contrast enhancer in a biofilm context, or for 3D imaging, or for bacteria. Note: although not used for visualizing bacteria or biofilms potassium permanganate is used sometimes to kill bacteria and algae, much like bleach is used.

It should be noted that since the principal ingredient, potassium permanganate, is an oxidizer, care must be taken not to apply for too long since over-exposure may result in lysing of the bacterial cells. Two minutes is an optimal time, although individuals may have to establish an optimal time specific to their own system. However, the reaction can be readily quenched by rinsing.

The mechanism of action is illustrated in FIG. 1.

There are no publications documenting the use of potassium permanganate to stain biofilms for conventional and 3D imaging. Potassium permanganate has been used as a counterstain in a fluorescent stain kit for acid fast organisms such as *Mycobacterium tuberculosis* (the infectious agent for TB). However, in this instance, potassium permanganate is used to stain the human background material associated with the *Mycobacterium tuberculosis* infections such as sputum or other human tissue, NOT the bacteria themselves. Potassium permanganate has not been previously applied to directly stain bacteria themselves. To facilitate the utility of such a staining, REFLECTED confocal imaging is used, rather than the conventional FLUORESCENCE confocal imaging to visualize the potassium permanganate stained matrix in 3D.

Method for Staining Biofilm EPS for Fluorescent Microscopy:

7) Preserve biofilm structure using a conventional method such as formaldehyde, paraformaldehyde, gluteraldehyde or any standard fixative. However, this step is not necessary for staining biofilms, and in fact aldehydes such as formaldehyde, paraformaldehyde and gluteraldehyde are known to not be particularly effective at preserving EPS (Hunter and Beveridge 2005) and in fact are used to dissolve and extract carbohydrates in biofilm EPS (Zhang et al. 1999). When fluorescence based viability staining is required (for example with Molecular Probes BacLight Live/Dead kit (Molecular Probes) immerse biofilm in component "A" of the Biofilm EPS Contrast Enhancer. This composition is a modification of "Hanks balanced salts solution" (without D-glucose and phenol red) (Hank 1949). Incubate at room temperature for 10 minutes. This step removes loosely adhered bacterial cells and strengthens the biofilm EPS by cross-linking anionic charges in EPS (Stoodley et al. 2001). Note: it is possible that a trivalent cation such as aluminum chloride ($AlCl_3$) would be more efficient at cross-linking (Stoodley et al. 2001).

| Component "A" of the Biofilm EPS Contrast Enhancer. | |
| --- | --- |
| Component | G/L |
| $CaCl_2$ | 0.14 |
| KCl | 0.4 |
| $KH2PO_4$ | 0.06 |
| $MgCl_2 \cdot 6H_2O$ | 0.1 |
| $MgSO_4 \cdot 7H_2O$ | 0.1 |
| NaCl | 8.0 |
| $NaHCO_3$ | 0.35 |
| $Na_2HPO_4 \cdot 7H_2O$ | 0.09 |

NOTE
COMPONENT "A" is based on the ingredient list for the commercially available Hanks solution.

8) Add a few drops of Component "B" of the Biofilm EPS Contrast Enhancer. (1% potassium permanganate solution in water) so that there is complete coverage of the biofilm. NOTE it may be possible to optimize the concentration and incubation time.
9) Incubate at room temperature for 2 minutes.
10) Rinse with Component "A" of the Biofilm EPS Contrast Enhancer. To stop the reaction and remove excess potassium permanganate.
11) Sample is now ready for microscopy. The use of a long working distance water immersion objective is recommended for hydrated samples.
12) The specimens can now be observed with confocal microscopy. Leica DM RXE microscope attached to a TCS SP2 AOBS confocal system (Leica Microsystems, Exton, Pa.) and a 63× water immersion objective for imaging was used. It should be noted that any confocal should work. Also, any light or combined light/fluorescence microscope will work.
13) The biofilm was observed using the 488 and 543 nm laser lines operating in sequential scanning mode. Live bacterial cells in the biofilm were observed by capturing fluorescent light emitted by the stain SYTO 9 fluorophore so that these bacteria appeared green. Dead (or more specifically membrane compromised) bacterial cells in the biofilm were observed by capturing fluorescent light emitted by the stain propidium iodide fluorophore so that these bacteria appeared red. (This step is not necessary to observe the EPS but rather shows colocalization with biofilm cells within the EPS as stained with the fluorescent nucleic acid markers.
14) The EPS was imaged by collecting the reflected signal from the 488 laser using the reflected signal from the laser using acoustico-optical beam splitter (AOBS) optimization so that the EPS appeared blue (FIG. 3D).
15) Each channel of the 3D confocal stacks can be quantified using COMSTAT (Heydorn et al. 2000) to determine the relative proportions of live and dead cells and EPS to the biofilm volume.
16) Image Analysis and COMSTAT analysis. The image analysis packages COMSTAT or Scion Image can be used to automatically quantify EPS. Using CLSM, it is also possible to construct 2-D and 3-D spatial maps of EPS. By using the EPS contrast enhancer in conjunction with fluorescent nucleic acid probes which yield red and/or green intensities, bacterial biofilms can be visualized the resolution of individual cells.

Method for Staining Biofilm EPS for 96 Well Plate Quantification.
1) Grow biofilms in multi-well plates as described by O'Toole et al. (Methods Enzymol. 1999).

2) After growth period, rinse biofilm with Component "A" of the Biofilm EPS Contrast Enhancer by replacing the growth medium. Repeat.
3) Stain biofilm by filling the well with Component "B" of the Biofilm EPS Contrast Enhancer for 2 minutes.
4) Rinse excess Component "A" of the Biofilm EPS Contrast Enhancer.
5) Quantify amount of biofilm using absorption with a plate reader.

Preliminary Data Supporting the Application of the Invention.

Example of COMSTAT data used to quantify the amount of biofilm assessed using the conventional staining based on staining just the bacterial cells and then with the signal from the Biofilm EPS Contrast Enhancer on three data stacks from two samples. The results are shown in the following Table (Table 2 of the original patent application).

TABLE 2

| | Average Thickness (μm) | | | Total volume of biofilm ($\mu m^3/\mu m^2$) | | |
|---|---|---|---|---|---|---|
| Strain | Without enhancer | With enhancer | Fold increase | Without enhancer | With enhancer | Fold increase |
| PAO1 | 2.9 | 6.5 | 2.2 | 0.7 | 2.4 | 3.4 |
| PAO1 | 0.9 | 3.4 | 3.8 | 0.1 | 0.9 | 9 |
| Pitt D | 2.5 | 12.3 | 4.9 | 0.3 | 1.3 | 4.3 |

With the Biofilm EPS Contrast Enhancer, there was between three to nine times the amounts of biofilm in terms of volume than would have been measured using conventional staining, demonstrating that in these samples most of the biofilm would have gone undetected.

Example

Biofilms of *Pseudomonas aeruginosa*, a common pathogen in many human infections, were grown in glass bottomed Petri dishes for between 2 to 5 days at 37° C. on LB medium. Biofilms were grown from a clinical isolate from a child with otitis externa (PittD) as well as a reference strain from ATTC (PAO1). After the growth period the biofilms were stained with Molecular Probes BacLight™ Live/Dead viability kit (Invitrogen) according to manufacturer instructions. The samples were then stained with the Biofilm EPS Contrast Enhancer as described above. The specimens were then observed with confocal microscopy using a Leica DM RXE microscope attached to a TCS SP2 AOBS confocal system (Leica Microsystems, Exton, Pa.). A 63× water immersion objective was used for imaging. The biofilm was observed using the 488 and 543 nm laser lines operating in sequential scanning mode. Live bacterial cells in the biofilm were observed by capturing fluorescent light emitted by the stain SYTO® 9 fluorophore so that these bacteria appeared green. Dead (or more specifically membrane compromised) bacterial cells in the biofilm were observed by capturing fluorescent light emitted by the stain propidium iodide fluorophore so that these bacteria appeared red. The EPS was imaged by collecting the reflected signal from the 488 laser using the AOBS optimization so that the EPS appeared blue. Each channel of the 3D confocal stacks were quantified using COMSTAT (Heydorn et al. 2000) to determine the relative proportions of live and dead cells and EPS to the biofilm volume.

Figure 2:
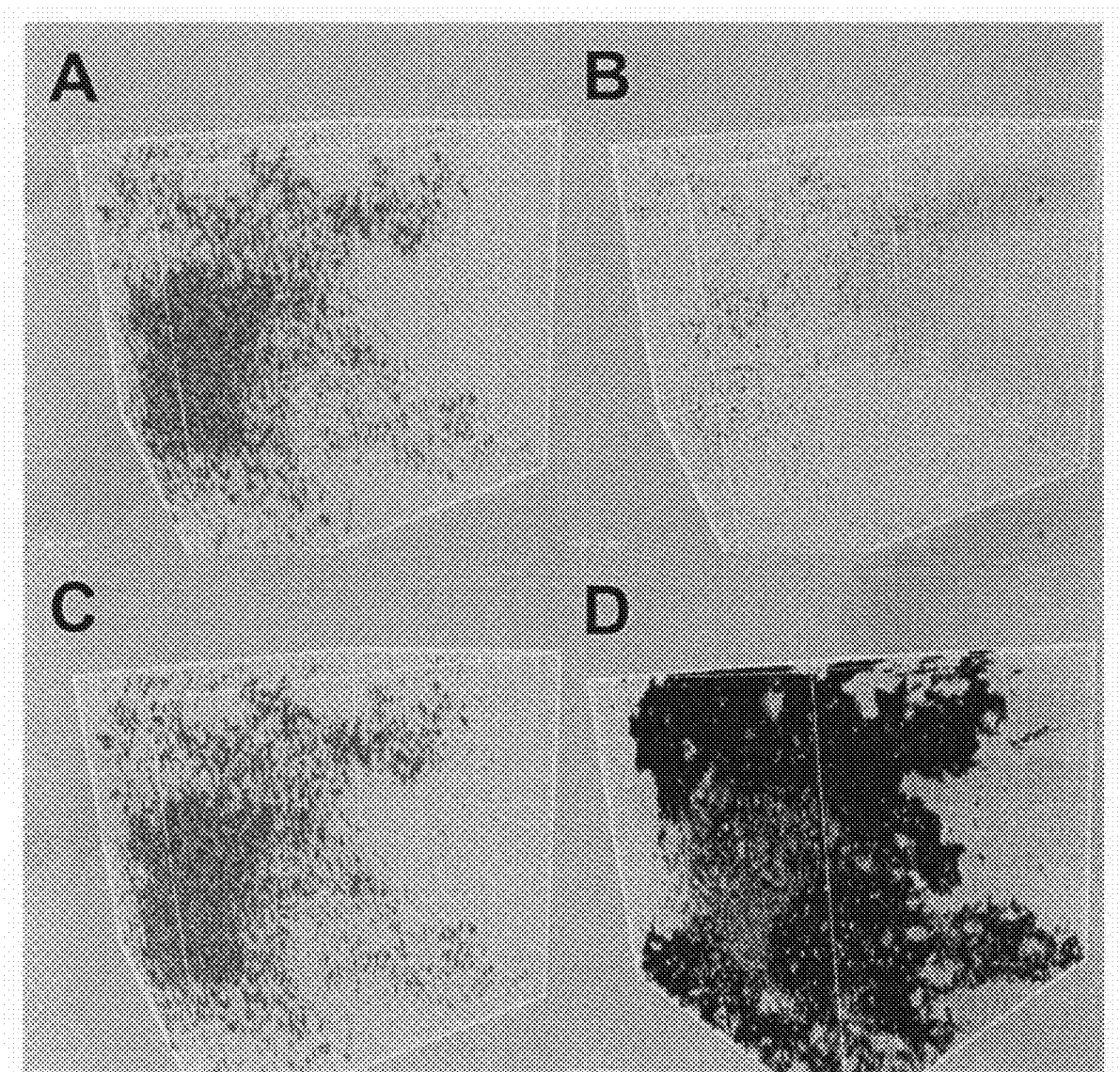
FIG. 2 shows a biofilm strained with the present invention.

The live and dead cells were clearly visible in the biofilm (FIG. 2) and the images were similar to those obtained by other researchers (Heydorn et al. 2000). However, the voluminous amount of EPS, which is normally invisible, could now be clearly observed (FIG. 2). In a few areas in the biofilm there patches which did not stain strongly with the Biofilm EPS Contrast Enhancer. However, in these areas the space between the bacterial cells was diffusely stained with the nucleic acid stain SYTO® 9 suggesting that in these areas the extracellular DNA may have been the principal component of the EPS (Whitchurch et al. 2002). It is possible that the Biofilm EPS Contrast Enhancer reacts more strongly with polysaccharides and proteins than nucleic acids. With the PAO1 biofilm the Biofilm EPS Contrast Enhancer revealed a complex web pattern of EPS connected the individual cells within the biofilm (FIG. 3). This structure would have gone undetected by conventional staining. Patches of cells were also found to be connected by EPS (FIG. 4).

In regard to FIG. 1:

Step 1—Biofilm composed of bacterial cells encapsulated in an EPS slime matrix.

Step 2—Cells in biofilm made fluorescent, the EPS remains invisible.

Step 3—Calcium and magnesium strengthen the biofilm, helping to preserve the structure. These ions have two positive charges. One of the divalent positive charges sticks to a negative charge on one polymer strand and the other sticks to a negative charge on another polymer strand (red bonds) binding them together. This phenomenon is called "cross-linking."

Step 4—The potassium permanganate oxidizes the EPS so it appears brown. The oxidized EPS gives a strong reflected signal for 3D confocal and other microscopic imaging. The bacterial cells remain fluorescent if stained with a fluorophore.

FIG. 2. *Pseudomonas aeruginosa* PittD biofilm stained with Molecular Probes BacLight™ Live/Dead viability kit and the Biofilm EPS Contrast Enhancer. A) Live cells fluoresce green from staining with SYTO® 9. B) Dead cells fluoresce red with propidium iodide. C) Live and dead staining of cells provide a "conventional" view of the biofilm. D) Biofilm EPS Contrast Enhancer shows extensive amount of EPS (here shown in blue).

FIG. 3. PAO1 biofilm stained with SYTO® 9 and Biofilm EPS Contrast Enhancer

The live/dead kit is listed as "LIVE/DEAD® BacLight™ Bacterial Viability Kit" The syto group of stains is listed as "SYTO®9". These can be purchased from Invitrogen.

FIG. 3A) Individual bacteria in the biofilm stained green with SYTO® 9. FIG. 3B) Biofilm EPS Contrast Enhancer revealed an otherwise invisible network of interconnecting EPS. FIG. 3C) Combined image showing the juxtaposition of the bacteria and the EPS.

FIG. 4. *P. aeruginosa* PittD biofilm stained with Molecular Probes BacLight™ Live/Dead viability kit and the Biofilm EPS Contrast Enhancer. Individual live bacterial cells within the biofilm stained green and dead cells stained red (in this case there were no dead cells). The voluminous EPS stained with the Biofilm EPS Contrast Enhancer using IMARIS™ (Bitplane Inc. www.bitplane.com) 3D rendering software (3D and 4D real-time interactive image visualization). The section in the foreground was made transparent (with IMARIS™) to reveal the distribution of bacteria within the EPS.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

APPENDIX

All of the following references are incorporated by referein herein.

Armstrong, A. R., and Price, N. E. (1947). Acid-fast bacilli in paraffin sections of tuberculous tissue. Canad. med. Ass. J., 56, 83-84.

Fite, G. L. (1938). The staining of acid-fast bacilli in paraffin sections. Amer. J. Path., 14, 491-507.

Kuper SWA, May JR. Detection of acid fast organisms in tissue sections by fluorescence microscopy. J Path Bact 1960; 79: 59-68

Commercially available product specifically designated for TB:
BBL Stain Kits BBL & DIFCO
TB Fluorescent Stain Kit T. One 250mL bottle each: Auramine − Rhodamine T, Decolorizer TM and Potassium Permanganate.

The following methods discuss stains (other than potassium permanganate) used for biofilm EPS:

Marrie TJ, Sung JY, Costerton JW. 1990. Bacterial biofilm formation on nasogastric tubes. *J Gastroenterol Hepatol.* 5(5):503-6.

Neu T, Swerhone GD, Lawrence JR. 2001. Assessment of lectin-binding analysis for in situ detection of glycoconjugates in biofilm systems. *Microbiology.* 147(Pt 2):299-313.

Staudt C, Horn H, Hempel DC, Neu TR. 2004. Volumetric measurements of bacterial cells and extracellular polymeric substance glycoconjugates in biofilms. *Biotechnol Bioeng.* 88(5):585-92.

Strathmann M, Wingender J, Flemming HC. 2002. Application of fluorescently labelled lectins for the visualization and biochemical characterization of polysaccharides in biofilms of *Pseudomonas aeruginosa. J Microbiol Methods.* 50(3):237-48.

Whitchurch, C., Tolker-Nielsen, T., Ragas, P., Mattick, J. 2002. Extracellular DNA Required for Bacterial Biofilm Formation. Science. 295(5559):1487.

Strengthening of the biofilm using multivalent cationic cross-linking.

Chen X, Stewart PS. 2002. Role of electrostatic interactions in cohesion of bacterial biofilms. *Appl Microbiol Biotechnol.* 59(6):718-20.

Hanks, J.H. and Wallace R.E. 1949. Relation of oxygen and temperature in the preservation of tissues by refrigeration. *Proc. Soc. Exp. Biol. Med.*, 71:196.

Heydorn AA, Nielsen T, Hentzer M, Stenberg C, Giskov M, Ersboll BK, Molin S. 2000. Quantification of biofilm structure by the novel computer program. *Comstat Microbiology* 146:2395-2407.

Hunter, R.C. and Beveridge, T.J. 2005. High-Resolution Visualization of *Pseudomonas aeruginosa* PAO1 Biofilms by Freeze-Substitution Transmission Electron Microscopy Journal of Bacteriology. 187(22):7619-7630.

Korstgens V., Flemming H-C., Wingender J., Borchard W., 2001. Influence of calcium ions on the mechanical properties of a model biofilm of mucoid *Pseudomonas aeruginosa*. Wat. Sci. Technol. 43:49-57.

Stoodley P, Jacobsen A, Dunsmore BC, Purevdorj B, Wilson S, Lappin-Scott HM, Costerton JW. 2001. The influence of fluid shear and AICI3 on the material properties of *Pseudomonas aeruginosa* PAO1 and *Desulfovibrio* sp. EX265 biofilms. *Water Sci Technol.* 43(6):113-20.

Whitchurch, C., Tolker-Nielsen, T., Ragas, P., Mattick, J. 2002. Extracellular DNA Required for Bacterial Biofilm Formation. Science. 295(5559):1487.

Zhang, X., Bishop, P. L., Kinkle, B. K. (1999) Comparison of extraction methods for quantifying extracellular polymers in biofilms. Wat. Sci. Tech. 39:211-218.

The invention claimed is:

1. A method for preparing a biofilm such that the biofilm can be visualized comprising the steps of:
   staining bacterial cells in the biofilm with a fluorophore;
   staining the biofilm with a stain containing potassium permanganate and water;
   incubating the biofilm with the stains
   rinsing the biofilm to remove potassium permanganate the stain; and
   visualizing cells and extracellular polymeric substance of the biofilm using reflected confocal microscopy.

2. A method as described in claim 1 wherein the rinsing step includes the step of rinsing with a solution of $CaCl_2$, KCl, $KH_2PO_4$, $MgCl_2.6H_2O$, $MgSO_4.7H_2O$, NaCl, $NaHCO_3$, and $Na_2HPO_4.7H2O$.

3. A method as described in claim 1, further comprising the step of growing the biofilm in a multi-well plate format or flow cell format or biofilm reactor.

4. A method as described in claim 1, further comprising the step of quantifying the amount of biofilm.

5. The method of claim 4, wherein quantifying the amount of biofilm comprises determining the thickness of the biofilm or determining the total volume of the biofilm.

6. A method as described in claim 1, wherein the visualizing step includes the step of visualizing cells in the biofilm by capturing fluorescent light.

7. A method as described in claim 6 wherein the visualizing step includes the step of visualizing the cells with laser lines operating in sequential scanning mode.

8. A method as described in claim 1, wherein the visualizing step includes the step of visualizing the biofilm in 3D.

9. The method of claim 1, wherein the rinsing step comprising immersing the biofilm in a rinse fluid and incubating the biofilm.

* * * * *